United States Patent
Hatlestad et al.

(10) Patent No.: US 8,818,748 B2
(45) Date of Patent: *Aug. 26, 2014

(54) POSTURE SENSOR AUTOMATIC CALIBRATION

(75) Inventors: John D. Hatlestad, Maplewood, MN (US); Aaron Lewicke, Forest Lake, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/437,374

(22) Filed: Apr. 2, 2012

(65) Prior Publication Data

US 2012/0191155 A1 Jul. 26, 2012

Related U.S. Application Data

(63) Continuation of application No. 12/425,195, filed on Apr. 16, 2009, now Pat. No. 8,165,840.

(60) Provisional application No. 61/060,987, filed on Jun. 12, 2008.

(51) Int. Cl.
| | | |
|---|---|---|
| *G01P 21/00* | (2006.01) | |
| *G01C 22/00* | (2006.01) | |
| *G01C 25/00* | (2006.01) | |
| *G01D 18/00* | (2006.01) | |
| *G06F 19/00* | (2006.01) | |
| *G06F 17/40* | (2006.01) | |

(52) U.S. Cl.
CPC .............. *G01P 21/00* (2013.01); *G01C 22/00* (2013.01); *G01C 25/00* (2013.01); *G01D 18/00* (2013.01); *G06F 19/00* (2013.01); *G06F 17/40* (2013.01)
USPC ............. 702/85; 73/1.38; 73/382 R; 702/104; 702/187; 702/189

(58) Field of Classification Search
CPC ...... G01C 22/00; G01C 22/006; G01C 25/00; G01P 13/00; G01P 21/00; G06F 11/00; G06F 11/30; G06F 11/32; G06F 17/00; G06F 17/40; G06F 19/00
USPC .......... 73/1.01, 1.37, 1.38, 1.75, 1.77, 382 R, 73/382 G, 432.1, 865.8, 865.9; 702/1, 33, 702/56, 85, 92, 94, 104, 127, 141, 150, 187, 702/189
IPC ........ G01C 22/00, 22/006, 25/00; G01D 18/00; G01P 13/00, 21/00; G06F 11/00, 11/30, 11/32, G06F 17/00, 17/40, 19/00
See application file for complete search history.

(56) References Cited

U.S. PATENT DOCUMENTS

| | | |
|---|---|---|
| 4,846,195 A | 7/1989 | Alt et al. |
| 4,869,251 A | 9/1989 | Lekholm et al. |

(Continued)

FOREIGN PATENT DOCUMENTS

| | | |
|---|---|---|
| EP | 0804939 A2 | 11/1997 |
| WO | WO-9502431 A1 | 1/1995 |

(Continued)

OTHER PUBLICATIONS

"Abbott Diagnostics—Heart Failure", Abbott Laboratories, Abbott Park Illinois, (2011), 8 pgs.

(Continued)

*Primary Examiner* — Edward Cosimano
(74) *Attorney, Agent, or Firm* — Schwegman, Lundberg & Woessner, P.A.

(57) ABSTRACT

A system and method automatically calibrate a posture sensor, such as by detecting a walking state or a posture change. For example, a three-axis accelerometer can be used to detect a patient's activity or posture. This information can be used to automatically calibrate subsequent posture or acceleration data.

20 Claims, 7 Drawing Sheets

(56) References Cited

U.S. PATENT DOCUMENTS

| | | |
|---|---|---|
| 5,010,893 A | 4/1991 | Sholder |
| 5,031,618 A | 7/1991 | Mullett |
| 5,233,984 A | 8/1993 | Thompson |
| 5,330,505 A | 7/1994 | Cohen |
| 5,354,317 A | 10/1994 | Alt |
| 5,593,431 A | 1/1997 | Sheldon |
| 5,725,562 A | 3/1998 | Sheldon |
| 5,957,957 A | 9/1999 | Sheldon |
| 6,021,352 A | 2/2000 | Christopherson et al. |
| 6,044,297 A | 3/2000 | Sheldon et al. |
| 6,045,513 A | 4/2000 | Stone et al. |
| 6,102,874 A | 8/2000 | Stone et al. |
| 6,246,910 B1 | 6/2001 | Bonnet et al. |
| 6,270,457 B1 | 8/2001 | Bardy |
| 6,273,856 B1 | 8/2001 | Sun et al. |
| 6,280,409 B1 | 8/2001 | Stone et al. |
| 6,336,903 B1 | 1/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,466,821 B1 | 10/2002 | Pianca et al. |
| 6,473,646 B2 | 10/2002 | Sun et al. |
| 6,539,249 B1 | 3/2003 | Kadhiresan et al. |
| 6,572,557 B2 | 6/2003 | Tchou et al. |
| 6,600,941 B1 | 7/2003 | Khuri |
| 6,658,292 B2 | 12/2003 | Kroll et al. |
| 6,694,186 B2 | 2/2004 | Bardy |
| 6,704,595 B2 | 3/2004 | Bardy |
| 6,741,885 B1 | 5/2004 | Bornzin et al. |
| 6,811,537 B2 | 11/2004 | Bardy |
| 6,826,425 B2 | 11/2004 | Bardy |
| 6,827,690 B2 | 12/2004 | Bardy |
| 6,834,436 B2 | 12/2004 | Townsend et al. |
| 6,887,201 B2 | 5/2005 | Bardy |
| 6,904,312 B2 | 6/2005 | Bardy |
| 6,908,437 B2 | 6/2005 | Bardy |
| 6,913,577 B2 | 7/2005 | Bardy |
| 6,937,900 B1 | 8/2005 | Pianca et al. |
| 6,945,934 B2 | 9/2005 | Bardy |
| 6,952,611 B2 | 10/2005 | Sun et al. |
| 6,961,615 B2 | 11/2005 | Kroll et al. |
| 6,974,413 B2 | 12/2005 | Bardy |
| 6,990,375 B2 | 1/2006 | Kloss et al. |
| 7,155,281 B1 | 12/2006 | Fayram |
| 7,171,271 B2 | 1/2007 | Koh et al. |
| 7,207,945 B2 | 4/2007 | Bardy |
| 7,210,240 B2 | 5/2007 | Townsend et al. |
| 7,258,670 B2 | 8/2007 | Bardy |
| 7,260,436 B2 | 8/2007 | Kilgore et al. |
| 7,299,087 B2 | 11/2007 | Bardy |
| 7,302,291 B2 | 11/2007 | Bardy |
| 7,313,440 B2 | 12/2007 | Miesel |
| 7,328,131 B2 | 2/2008 | Donofrio et al. |
| 7,471,290 B2 | 12/2008 | Wang |
| 7,636,602 B2 | 12/2009 | Baru Fassio et al. |
| 7,698,830 B2 | 4/2010 | Townsend et al. |
| 7,844,336 B2 | 11/2010 | Fricke et al. |
| 7,848,811 B2 * | 12/2010 | Moon et al. ............... 607/19 |
| 8,165,840 B2 * | 4/2012 | Hatlestad et al. ............ 702/104 |
| 8,366,641 B2 * | 2/2013 | Wang et al. ............... 600/595 |
| 2002/0151936 A1 | 10/2002 | Kloss et al. |
| 2002/0170193 A1 | 11/2002 | Townsend et al. |
| 2002/0188332 A1 | 12/2002 | Lurie et al. |
| 2003/0040776 A1 | 2/2003 | Kroll et al. |
| 2003/0149453 A1 | 8/2003 | Kroll et al. |
| 2004/0073128 A1 | 4/2004 | Hatlestad et al. |
| 2004/0112151 A1 | 6/2004 | Maxwell et al. |
| 2004/0127807 A1 | 7/2004 | Hatlesad et al. |
| 2005/0010265 A1 | 1/2005 | Baru et al. |
| 2005/0126026 A1 | 6/2005 | Townsend et al. |
| 2005/0245988 A1 | 11/2005 | Miesel |
| 2007/0115277 A1 | 5/2007 | Wang et al. |
| 2007/0118056 A1 | 5/2007 | Wang et al. |
| 2007/0142868 A1 * | 6/2007 | Moon et al. ............... 607/19 |
| 2007/0169364 A1 | 7/2007 | Townsend et al. |
| 2007/0293741 A1 | 12/2007 | Bardy |
| 2008/0082001 A1 | 4/2008 | Hatlestad et al. |
| 2008/0255626 A1 | 10/2008 | Fricke et al. |
| 2009/0024005 A1 | 1/2009 | Lewicke et al. |
| 2009/0227883 A1 | 9/2009 | Zhang et al. |
| 2009/0312973 A1 | 12/2009 | Hatlestad et al. |
| 2011/0046520 A1 | 2/2011 | Fricke et al. |
| 2013/0207889 A1 * | 8/2013 | Chang et al. ............... 345/156 |
| 2013/0298636 A1 * | 11/2013 | Hatlestad et al. ............ 73/1.38 |

FOREIGN PATENT DOCUMENTS

| | | |
|---|---|---|
| WO | WO-0189365 A2 | 11/2001 |
| WO | WO-2009110996 A1 | 9/2009 |

OTHER PUBLICATIONS

"U.S. Appl. No. 10/892,937, Final Office Action mailed Mar. 11, 2010", 7 pgs.

"U.S. Appl. No. 10/892,937, Final Office Action mailed Oct. 13, 2011", 6 pgs.

"U.S. Appl. No. 10/892,937, Non-Final Office Action mailed Apr. 28, 2011", 6 pgs.

"U.S. Appl. No. 10/892,937, Non-Final Office Action mailed Feb. 3, 2009", 8 pgs.

"U.S. Appl. No. 10/892,937, Notice of Allowance mailed Jan. 25, 2012", 5 pgs.

"U.S. Appl. No. 10/892,937, Response filed Jan. 13, 2012 to Final Office Action mailed Oct. 13, 2011", 5 pgs.

"U.S. Appl. No. 10/892,937, Response filed May 4, 2009 to Non-Final Office Action mailed Feb. 3, 2009", 7 pgs.

"U.S. Appl. No. 10/892,937, Response filed Jun. 11, 2010 to Final Office Action mailed Mar. 11, 2010", 6 pgs.

"U.S. Appl. No. 10/892,937, Response filed Aug. 29, 2011 to Non-Final Office Action mailed Apr. 28, 11", 6 pgs.

"U.S. Appl. No. 11/733,663, Final Office Action mailed May 19, 2010", 8 pgs.

"U.S. Appl. No. 11/733,663, Non-Final Office Action mailed Dec. 10, 2009", 5 pgs.

"U.S. Appl. No. 11/733,663, Notice of Allowance mailed Jul. 23, 2010", 6 pgs.

"U.S. Appl. No. 11/733,663, Response filed Mar. 9, 2010 to Non Final Office Action mailed Dec. 10, 2009", 9 pgs.

"U.S. Appl. No. 11/733,663, Response filed Jun. 22, 2010 to Final Office Action mailed May 19, 2010", 11 pgs.

"U.S. Appl. No. 12/396,196, Appeal Brief filed Jan. 8, 2012", 32 pgs.

"U.S. Appl. No. 12/396,196, Decision on Pre-Appeal Brief Request mailed Dec. 7, 2011", 2 pgs.

"U.S. Appl. No. 12/396,196, Examiner's Answer mailed Feb. 27, 2012", 13 pgs.

"U.S. Appl. No. 12/396,196, Final Office Action mailed Aug. 2, 2011", 9 pgs.

"U.S. Appl. No. 12/396,196, Non-Final Office Action mailed Mar. 11, 2011", 8 pgs.

"U.S. Appl. No. 12/396,196, Pre-Appeal Brief Request filed Oct. 3, 2011", 5 pgs.

"U.S. Appl. No. 12/396,196, Response filed Jun. 13, 2011 to Non-Final Office Action mailed Mar. 11, 2011", 10 pgs.

"U.S. Appl. No. 12/425,195, Ex Parte Quayle Action mailed Oct. 12, 2011", 14 pgs.

"U.S. Appl. No. 12/425,195, Notice of Allowance mailed Dec. 19, 2011", 11 pgs.

"U.S. Appl. No. 12/425,195, Response filed Nov. 23, 2011 to Ex Parte Quayle Action mailed Dec. 12, 2011", 16 pgs.

"U.S. Appl. No. 12/912,077, Final Office Action mailed Mar. 13, 2012", 8 pgs.

"U.S. Appl. No. 12/912,077, Non Final Office Action mailed Nov. 1, 2011", 7 pgs.

"U.S. Appl. No. 12/912,077, Response filed Jan. 31, 2012 to Non-Final Office Action mailed Nov. 11, 2011", 12 pgs.

"International Application Serial No. PCT/US2009/001314, International Search Report mailed Jul. 20, 2009", 4 pgs.

"International Application Serial No. PCT/US2009/001314, Written Opinion mailed Jul. 20, 2009", 7 pgs.

(56) References Cited

OTHER PUBLICATIONS

Arvanitakis, Z., et al., "Diabetes mellitus and progression of rigidity and gait disturbance in older persons", Neurology, 63(6), (2004), 996-1001.

Evangelista, Lorraine S., et al., "Validity of Pedometers for Measuring Exercise Adherence in Heart Failure Patients", Journal of Cardiac Failure, 11(5), (2005), 366-71.

Fleg, J. L, et al., "Assessment of functional capacity in clinical and research applications: An advisory from the Committee on Exercise, Rehabilitation, and Prevention, Council on Clinical Cardiology, American Heart Association", Circulation, 102(13), (Sep. 26, 2000), 1591-7.

Hunt, S. A, et al., "ACC/AHA Guidelines for the Evaluation and Management of Chronic Heart Failure in the Adult: Executive Summary A Report of the American College of Cardiology/American Heart Association Task Force on Practice Guidelines", Circulation., 104(24), (Dec. 11, 2001), 2996-3007.

Mai, J., et al., "Posture Detection Algorithm Using Multi Axis DC Accelerometer", PACE, vol. 22 (Part II), (Abstract #605), (Apr. 1999), p. 851.

Mancini, D. M., et al., "Value of peak exercise oxygen consumption for optimal timing of cardiac transplantation in ambulatory patients with heart failure", Circulation, 83(3), (1991), 778-86.

Schneider, Patrick L, et al., "Accuracy and reliability of 10 pedometers for measuring steps over a 400-m walk", Medicine and Science in Sports and Exercise, 35(10), (2003), 1779-1784.

Schneider, Patrick L, et al., "Pedometer measures of Free-Living Physical Activity: Comparison of 13 Models", Medicine and Science in Sports and Exercise, 36(2), (2004), 331-335.

Thompson, D. L, et al., "Relationship between Accumulated Walking and body Composition in Middle-Aged Women", Medicine and Science in Sports and Exercise, 36(5), (2004), 911-914.

Walsh, J T, et al., "Relation of daily activity levels in patients with chronic heart failure to long-term prognosis", Am J Cardiol, 79(10), (1997), 1364-1369.

Weber, K. T., et al., "Oxygen utilization and ventilation during exercise in patients with chronic cardiac failure", Circulation, 65(6), (Jun. 1982), 1213-23.

* cited by examiner

POSTURE SENSOR AUTOMATIC CALIBRATION

CROSS-REFERENCE TO RELATED APPLICATION

This application is a continuation of and claims the benefit of priority under 35 U.S.C. §120 to U.S. patent application Ser. No. 12/425,195, filed on Apr. 16, 2009, now U.S. Pat. No. 8,165,840, which claims the benefit of priority of expired U.S. Provisional Application Ser. No. 61/060,987, filed on Jun. 12, 2008, under 35 U.S.C. §119(e), which is hereby incorporated by reference.

BACKGROUND

Cardiac rhythm management devices are used to monitor and treat cardiac patients. Acceleration is one possible input for a cardiac rhythm management device.

OVERVIEW

This document describes, among other things, a system and method for automatically calibrating a posture sensor, such as by detecting a walking state or a posture change. For example, a three-axis accelerometer can be used to detect a patient's activity or posture. This information can be used to automatically calibrate subsequent posture or acceleration data.

Example 1 describes a method. In this example, the method comprises sensing an acceleration signal from a patient using an accelerometer; detecting a walking state using the acceleration signal, the detecting the walking state including: extracting a characteristic of an AC component of the acceleration signal; performing a comparison between the characteristic and a template; and using the comparison to distinguish the walking state from a non-walking activity state; and using an orientation of the accelerometer in the walking state to perform a posture calibration of the acceleration signal of the accelerometer.

In Example 2, the method of Example 1 optionally comprises sensing an acceleration signal from a patient using an accelerometer by sensing an acceleration signal from an implantable accelerometer when implanted in the patient.

In Example 3, the method of one or any combination of Examples 1-2 optionally comprises computing a DC component of the acceleration signal; determining a gravity vector using the DC component of the acceleration signal; computing a parallel component of the acceleration signal, the parallel component being in the direction of the gravity vector; computing an orthogonal component of the acceleration signal, the orthogonal component being in a direction orthogonal to the gravity vector; wherein the performing the comparison comprises comparing the parallel component to a parallel template and comparing the orthogonal component to an orthogonal template; and wherein the using the comparison to distinguish the walking state from the non-walking activity state comprises using the computed parallel component of the acceleration signal and using the computed orthogonal component of the acceleration signal.

In Example 4, the method of one or any combination of Examples 1-3 optionally comprises using the comparison to distinguish the walking state from the non-walking activity state by comparing the parallel comparison to a first threshold value and comparing the orthogonal comparison to a second threshold value.

In Example 5, the method of one or any combination of Examples 1-4 optionally comprises computing the DC component of the acceleration signal by computing a DC component of the acceleration signal in each of orthogonal x, y, and z directions of the accelerometer; and determining a gravity vector by determining a three dimensional gravity vector using the DC component of the acceleration signal in each of x, y, and z directions of the accelerometer.

In Example 6, the method of one or any combination of Examples 1-5 optionally comprises using the comparison to distinguish the walking state from the non-walking activity state by: determining a central tendency of the gravity vectors; comparing the central tendency of the gravity vectors to a previously-determined central tendency of the gravity vectors; and determining whether the gravity vectors are consistent using a difference between the central tendency of the gravity vectors and the previously-determined central tendency of the gravity vectors.

In Example 7, the method of one or any combination of Examples 1-6 optionally comprises performing a comparison between the characteristic and a template by performing the comparison between at least one of: a frequency-domain characteristic and a frequency-domain template; a time-domain characteristic and a time-domain template; and a time-frequency-domain characteristic and a time-frequency-domain template.

In Example 8, the method of one or any combination of Examples 1-7 optionally comprises using the comparison to distinguish the walking state from a non-walking activity state by comparing the comparison to a threshold value.

Example 9 is a method that comprises sensing an acceleration signal from a patient using an accelerometer; sensing a first steady state posture from the acceleration signal; calculating a first gravity vector orientation of plurality of gravity vectors detected from the acceleration signal during a first time period and in the first steady state posture; detecting a second gravity vector orientation that differs from the first gravity vector orientation by at least a threshold value; detecting a second steady state posture associated with the second gravity vector orientation; and upon detecting the second steady state posture associated with the second gravity vector orientation, automatically performing a calibration using a plurality of gravity vectors associated with only one of either the first or second steady state postures.

In Example 10, the method of Example 9 optionally comprises sensing an acceleration signal from a patient using an accelerometer by sensing an acceleration signal from an implantable accelerometer when implanted in the patient.

In Example 11, the method of one or any combination of Examples 9-10 optionally comprises sensing an acceleration signal from a patient using an accelerometer by determining a DC component of the acceleration signal; and detecting a second steady state posture associated with the second gravity vector orientation comprises detecting a change in orientation between the first gravity vector orientation and the second gravity vector orientation, the change in orientation being above a specified threshold value for at least a specified second time period.

In Example 12, the method of one or any combination of Examples 9-11 optionally comprises calculating a first gravity vector orientation of plurality of gravity vectors detected from the acceleration signal during a first time period and in the first steady state posture by determining a consistency of the first gravity vector orientation during the first time period; and detecting a second steady state posture associated with the second gravity vector orientation comprises determining a consistency of the second gravity vector orientation during the second time period; and when the first and second gravity vector orientations are deemed consistent, using a central tendency of one of the consistent first and second gravity vector orientations to perform a posture calibration of the acceleration signal of the accelerometer.

In Example 13, the method of one or any combination of Examples 9-12 optionally comprises sensing an acceleration signal from a patient by computing a DC component of the acceleration signal in each of orthogonal x, y, and z directions of the accelerometer.

In Example 14, the method of one or any combination of Examples 9-13 optionally comprises determining a consistency of the first or second gravity vector orientations during the first time period by: determining a central tendency of the gravity vectors; comparing the central tendency of the gravity vectors to a previously-determined central tendency of the gravity vectors; and determining whether the gravity vectors are consistent using a difference between the central tendency of the gravity vectors and the previously-determined central tendency of the gravity vectors.

In Example 15, the method of one or any combination of Examples 9-14 optionally comprises determining a consistency of the first or second gravity vector orientations during the first time period by: determining a dispersion of the gravity vectors; and determining whether the gravity vectors are consistent using a comparison of the dispersion to a specified dispersion threshold value.

In Example 16, the method of one or any combination of Examples 9-15 optionally comprises computing the specified dispersion threshold value using a previously-determined dispersion of the gravity vectors.

In Example 17, the method of one or any combination of Examples 9-16 optionally comprises identifying a posture during the first or second time period.

In Example 18, the method of one or any combination of Examples 9-17 optionally comprises identifying the posture during the first or second time period by using at least one of: a time of day for the identifying; a patient activity level for the identifying; and a physiologic sensor, of a different type than the accelerometer, for the identifying.

In Example 19, the method of one or any combination of Examples 9-18 optionally comprises determining the consistency of the first or second gravity vector orientations and, when the first or second gravity vector orientations are deemed inconsistent, performing the posture calibration without using the inconsistent gravity vectors.

Example 20 includes a device comprising an accelerometer, configured to sense an acceleration signal from a patient; and a signal processor circuit, coupled to the accelerometer, the signal processor circuit comprising or coupled to: a walking state detection circuit, configured to detect a walking state of the patient using the acceleration signal, the walking state detection circuit comprising: a highpass filter circuit, configured to extract an AC component of the acceleration signal, and further configured to extract a characteristic of the AC component of the acceleration signal; a stored template; a comparison circuit, coupled to the filter circuit and the template, the comparison circuit configured to perform a comparison between the characteristic and the template to distinguish the walking state from a non-walking activity state; and a posture calibration circuit, coupled to the comparison circuit, the posture calibration circuit configured to use the orientation of the accelerometer in the walking state to perform a posture calibration of the acceleration signal of the accelerometer.

In Example 21, the device of Example 20 optionally comprises an accelerometer that is implantable.

In Example 22, the device of one or any combination of Examples 20-21 optionally comprises a lowpass filter circuit, configured to compute a DC component of the acceleration signal; and the signal processor circuit configured to: determine a gravity vector using the DC component of the acceleration signal; compute a parallel component of the acceleration signal, the parallel component being in the direction of the gravity vector; compute an orthogonal component of the acceleration signal, the orthogonal component being in a direction orthogonal to the gravity vector; compare the parallel component to a parallel template and compare the orthogonal component to an orthogonal template; and distinguish the walking state from the non-walking activity state using the computed parallel component of the acceleration signal and using the computed orthogonal component of the acceleration signal.

In Example 23, the device of one or any combination of Examples 20-22 optionally comprises the signal processor circuit configured to distinguish the walking state from the non-walking activity state by: determining a central tendency of the gravity vectors; comparing the central tendency of the gravity vectors to a previously-determined central tendency of the gravity vectors; and determining whether the gravity vectors are consistent using a difference between the central tendency of the gravity vectors and the previously-determined central tendency of the gravity vectors.

In Example 24, the device of one or any combination of Examples 20-23 optionally comprises a stored domain template, the domain being at least one of frequency, time, and time-frequency; and the comparison circuit configured to perform a comparison between the characteristic and the domain template, wherein the characteristic comprises a domain characteristic.

Example 25 includes a device comprising an accelerometer, configured to sense an acceleration signal from a patient; and a signal processor circuit, coupled to the accelerometer, the signal processor circuit configured to: sense a first steady state posture from the acceleration signal; calculate a first gravity vector orientation of plurality of gravity vectors detected from the acceleration signal during a first time period and in the first steady state posture; detect a second gravity vector orientation that differs from the first gravity vector orientation by at least a threshold value; detect a second steady state posture associated with the second gravity vector orientation; and upon detecting the second steady state posture associated with the second gravity vector orientation, automatically perform a calibration using a plurality of gravity vectors associated with only one of either the first or second steady state postures.

In Example 26, the device of Example 25 optionally comprises an accelerometer that is implantable.

In Example 27, the device of one or any combination of Examples 25-26 optionally comprises a lowpass filter circuit, coupled to the accelerometer, configured to use the acceleration signal from the patient to determine a DC component of the acceleration; and the signal processor circuit configured to detect a second steady state posture associated with the second gravity vector orientation by detecting a change in orientation between the first gravity vector orientation and the second gravity vector orientation, the change in orientation being above a specified threshold value for at least a specified second time period.

In Example 28, the device of one or any combination of Examples 25-27 optionally comprises the signal processor circuit is configured to: determine a consistency of the first gravity vector orientation during the first time period; determine a consistency of the second gravity vector orientation during the second time period; and when the first and second gravity vector orientations are deemed consistent, use a central tendency of one of the consistent first and second gravity vector orientations to perform a posture calibration of the acceleration signal of the accelerometer.

In Example 29, the device of one or any combination of Examples 25-28 optionally comprises the signal processor being configured to determine a consistency of the first or second gravity vector orientations during the first time period by: determining a central tendency or a dispersion of the gravity vectors; and determining whether the gravity vectors are consistent using a comparison of the dispersion to a specified dispersion threshold value.

In Example 30, the device of one or any combination of Examples 25-29 optionally comprises the signal processor configured to identify a posture during the first or second time periods.

In Example 31, the device of one or any combination of Examples 25-30 optionally comprises the signal processor being configured to identify a posture during the first or second time periods using at least one of: a time of day; a patient activity level; and a physiologic sensor, of a different type than the accelerometer.

In Example 32, the device of one or any combination of Examples 25-31 optionally comprises the signal processor configured to perform the posture calibration, when the first or second gravity vector orientations are deemed inconsistent, without using the inconsistent gravity vectors.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe substantially similar components throughout the several views. Like numerals having different letter suffixes can represent different instances of substantially similar components. The drawings illustrate generally, by way of example, but not by way of limitation, various embodiments discussed in the present document.

DETAILED DESCRIPTION

This document describes, among other things, a system and method for automatically calibrating a posture sensor, such as by detecting a walking state or a posture change. Detecting such a state or posture, along with calculating a corresponding gravity vector, can be used to calibrate subsequent posture data.

Figure 1:
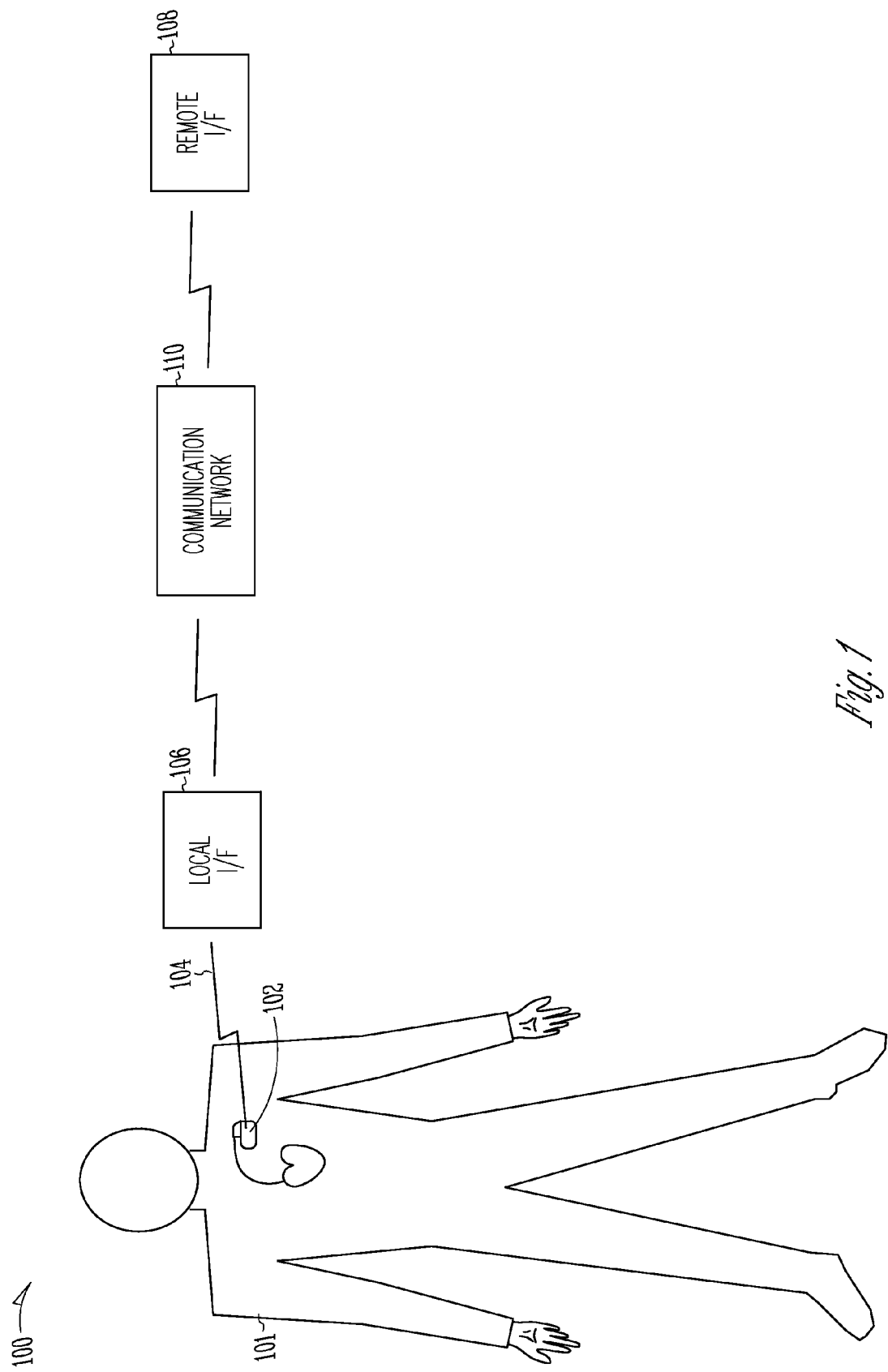
FIG. 1 is schematic diagram illustrating generally an example of a cardiac function management system, such as for use with a human or animal subject.

FIG. 1 is schematic diagram illustrating generally an example of a cardiac function management system 100, such as for use with a human subject 101. In this example, the system 100 includes an implantable or external cardiac function management device 102. The implantable or external cardiac function management device 102 can include or be communicatively coupled to an implantable or external posture-sensing accelerometer or other implantable or external posture sensing device. The cardiac function management device 102 can include a communication circuit, such as for establishing a bidirectional wireless communication link 104 with an external local interface 106, an implantable or external posture sensor, or other device with communication capability. In certain examples, the external local interface 106 can further bidirectionally communicate with an external remote interface 108, wirelessly or otherwise, such as via a shared communication or computer network 110.

Figure 2:
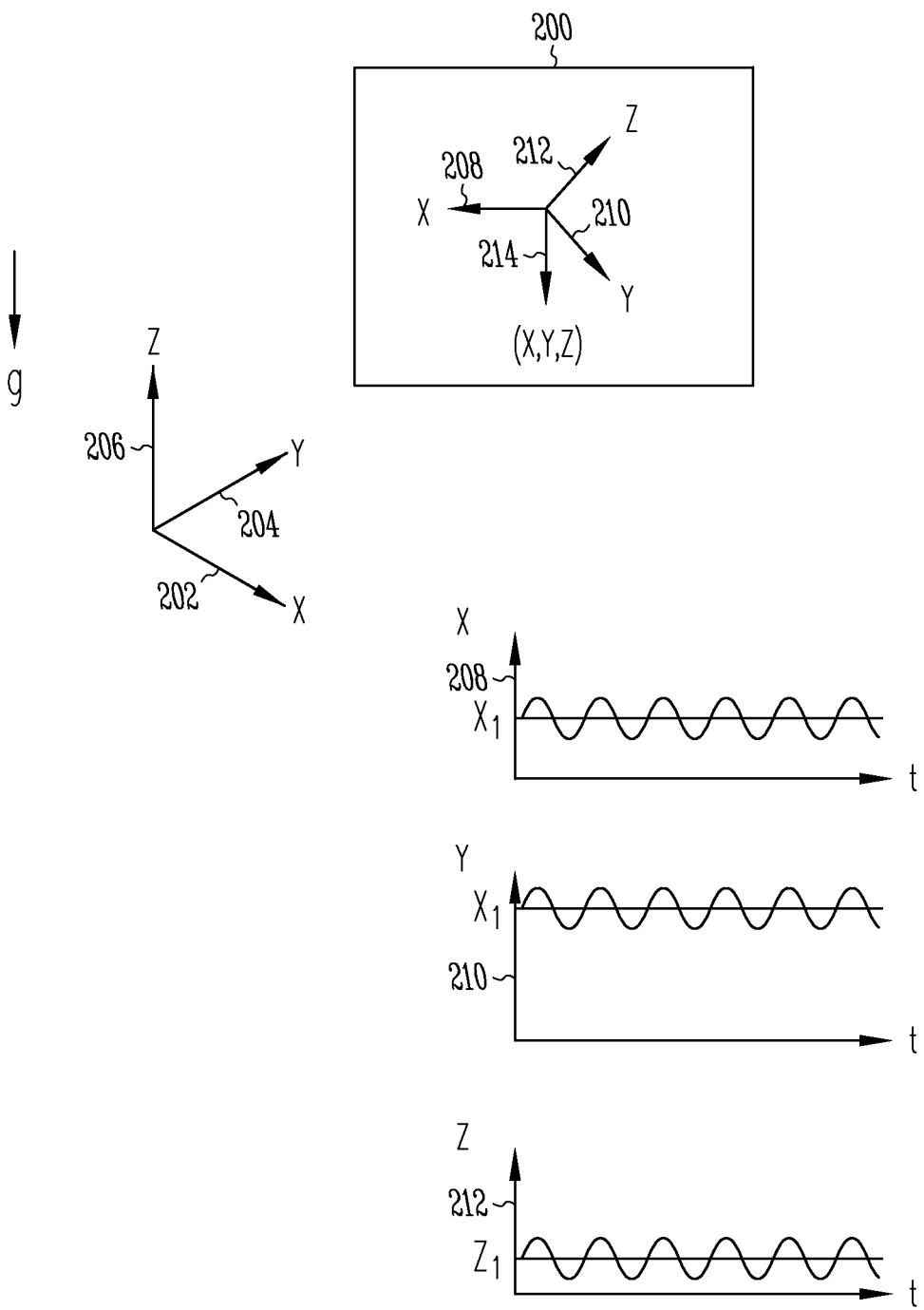
FIG. 2 is a set of diagrams illustrating generally an example of a three axis accelerometer system.

FIG. 2 is a set of diagrams illustrating generally an example of a three axis accelerometer system 200 located in three dimensional (3D) space that can be represented using an x-axis 202, a y-axis 204, and a z-axis 206. These axes can be oriented such that the force of gravity can be represented by a vector that is in the −z direction in the 3D space, opposite to the z-axis 206. The three axis accelerometer 200 can be used to output an acceleration signal that includes (1) an activity component indicative of a patient's physical activity; and (2) a posture component indicative of a patient's posture. In certain examples, it may be useful to calibrate the posture component of the three-axis accelerometer signal, such as by using information obtained in a particular ascertainable posture (e.g., standing, sitting, supine, left decubitus, right decubitus, etc.).

In an illustrative example of such calibration, accelerometer signal information can initially be used to hypothesize that a patient is in a "standing" posture, and then the accelerometer signal information in the standing posture can be used for automatically calibrating subsequent posture or other accelerometer information. Electrically transduced acceleration information (x, y, z) can be obtained from the x-axis 208, y-axis 210, and z-axis 212 electrical signal outputs of the three axis accelerometer 200, such as when the patient is in the hypothesized standing posture, over a first sampling time period. An average (or other central tendency) of the acceleration can be calculated for each of the x-axis 208, y-axis 210, and z-axis 212 over the first sampling time period, yielding a vector 214 (x1, y1, z1) that is indicative of the direction of gravity in the standing posture during the first sampling period. If the accelerometer were implanted perfectly upright, and the patient were standing perfectly upright, the vector 212 would have values (0, 0, z1=−g), where g=magnitude of acceleration of gravity. However, since the accelerometer may not have been implanted perfectly upright, and since the patient may not be standing perfectly upright, the vector 212 (x1, y1, and z1) will be different from (0, 0, z1=−g). A coordinate rotation vector can be calculated to represent the particular orientation of the accelerometer in the standing posture during the first sampling time period (see, e.g., Hua Wang and John Hatlestad U.S. patent application Ser. No. 11/283,490 (U.S. Patent App. Publication No. 20070118056, now U.S. Pat. No. 8,366,641, which is incorporated herein by reference in its entirety). The coordinate rotation vector can be used to calibrate subsequent posture data, so that such subsequent posture data can always be expressed relative to the orientation of the body.

Since there may be some movement or other postural variations in the standing posture, it can be useful to sample over one or more further sampling periods, such as a second sampling period, or over a longer first sampling period. In certain examples, a vector $(x2, y2, z2)$ is calculated over the second sampling period, or other further sampling periods, and a mean or other central tendency of the two vectors $(x1, y1, z1)$ and $(x2, y2, z2)$ can be computed over the various sampling periods before calculating a coordinate rotation vector between the mean or central tendency of the various sampled vectors and $(0, 0, z1=-g)$.

Figure 3:
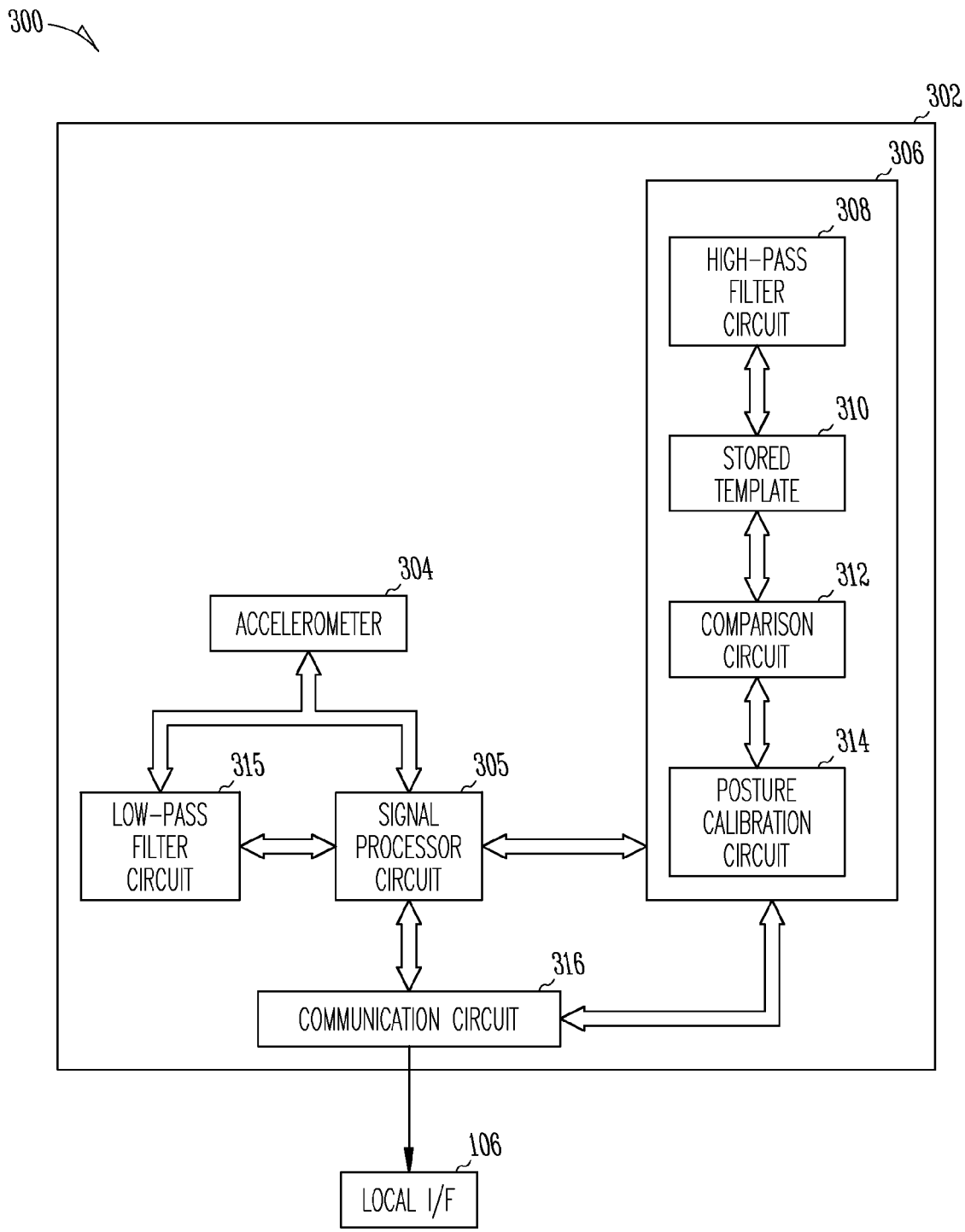
FIG. 3 is a block diagram illustrating generally an example of a system for automatically calibrating a posture sensor device by detecting a walking state.

FIG. 3 is a block diagram illustrating generally an example of a system 300 that can be used for automatically calibrating a posture sensor device 302, such as by detecting a walking state. The external or implantable posture sensor device 302 can be included in or communicatively coupled to an implantable or an external cardiac function management device 102. In this example, a three-axis accelerometer 304 can be configured to transduce an acceleration signal from a patient into an electrical or other signal that includes acceleration or posture information. The accelerometer 304 can be coupled to a signal processor circuit 305, which can include or be coupled to a low-pass filter circuit 315. The low-pass filter circuit 315 can be configured to compute a substantially DC component of the acceleration signal, such as when the detected acceleration signal is consistent with walking (e.g., walking is hypothesized). The signal processor circuit 305 can use information from the low-pass filter circuit 315 to determine a gravity vector using the DC components of the acceleration signal along the x-axis 208, y-axis 210, and z-axis 212 of the accelerometer. In order to determine the consistency of one or more such gravity vectors obtained in the walking state, the signal processor circuit 305 can determine a central tendency of the gravity vectors and can compare the central tendency to a previously-determined central tendency of the gravity vectors. A resulting difference between the between the central tendency of the gravity vectors and the previously-determined central tendency of the gravity vectors can be used to determine the consistency of the gravity vectors. In certain examples, when the gravity vectors are deemed consistent, the central tendency of the consistent gravity vectors can then be used to perform a calibration of the accelerometer.

In certain examples, once the gravity vectors are deemed consistent, the signal processor circuit 305 can compute (1) a parallel component of the acceleration signal in the direction of the gravity vector and (2) an orthogonal component of the acceleration signal in a direction orthogonal to the gravity vector. The signal processor circuit 305 can then compare the parallel component to a parallel template and the orthogonal component to an orthogonal template. Using the computed parallel and orthogonal components of the acceleration signal, the signal processor circuit 305 can further distinguish the walking state from the non-walking activity state.

Posture calibration can involve using a walking state detection circuit 306, which can be coupled to, or included within, the signal processor circuit 305. The walking state detection circuit 306 can be configured to detect a walking state of a patient using the acceleration signal. The waking state detection circuit 306 can include or be coupled to a highpass filter circuit 308, a stored template 310, a comparison circuit 312, and a posture calibration circuit 314. In certain examples, the highpass filter circuit 308 can be configured to extract an AC component of the acceleration signal, from which the signal processor circuit 305 can extract a characteristic of the AC component of the acceleration signal. The characteristic of the AC component extracted can include a frequency-domain characteristic, a time-domain characteristic, or a time-frequency-domain characteristic. In certain examples, one or more such characteristics can be separately extracted for the parallel component of the acceleration signal and the orthogonal component of the acceleration signal. Thus, examples of possible characteristics of an AC component extracted can include a parallel component frequency-domain characteristic, a parallel component time-domain characteristic, a parallel component time-frequency-domain characteristic, an orthogonal component frequency-domain characteristic, an orthogonal component time-domain characteristic, or an orthogonal component time-frequency-domain characteristic. One or more such extracted AC component characteristics can be compared to a corresponding stored template 310. The stored template 310 can include, in certain examples, one or more of a parallel component frequency-domain template, a parallel component time-domain template, a parallel component time-frequency-domain template, an orthogonal component frequency-domain template, an orthogonal component time-domain template, or an orthogonal component time-frequency-domain template. The comparison circuit 312 can be configured to perform a correlation or other comparison between a signal characteristic and its corresponding template. Using the result of the comparison, the signal processor circuit 305 can distinguish the walking state from a non-walking activity state. Information from the comparison circuit 312 can be communicated to the posture calibration circuit 314, which can perform posture calibration of the acceleration signal, such as described in Hua Wang and John Hatlestad U.S. patent application Ser. No. 11/283,490 (U.S. Pat. App. Publication No. 20070118056), now U.S. Pat. No. 8,366,641, which is incorporated herein by reference in its entirety, and Hua Wang et al. U.S. patent application Ser. No. 11/283,489 (U.S. Pat. App. Publication No. 20070115277) now U.S. Pat. No. 7,471,290, which is also incorporated herein by reference in its entirety. The posture calibration information can then be communicated to the communication circuit 316, such as for communicating with the local interface 106.

Figure 4:
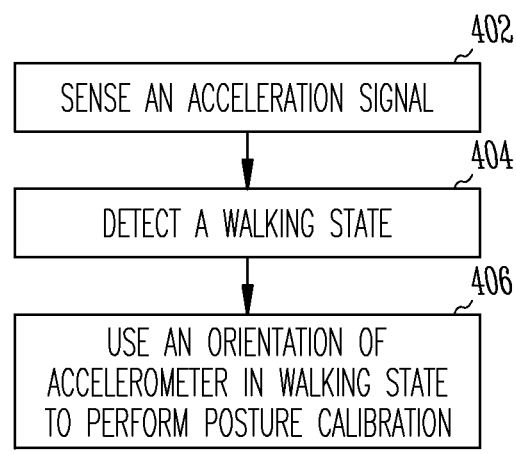
FIG. 4 is a flow chart illustrating an overview of an example of a method for performing posture calibration when a patient is in a walking state.

FIG. 4 is a flow chart illustrating an overview of an example of a method for performing posture calibration when a patient is in a walking state. At 402, an acceleration signal can be sensed from a patient, such as by using a three-axis accelerometer. The accelerometer can be implantable or external. At 404, a walking state can be detected using the acceleration signal. At 406, the orientation of the accelerometer in the walking state can be used to perform a posture calibration.

Figure 5:
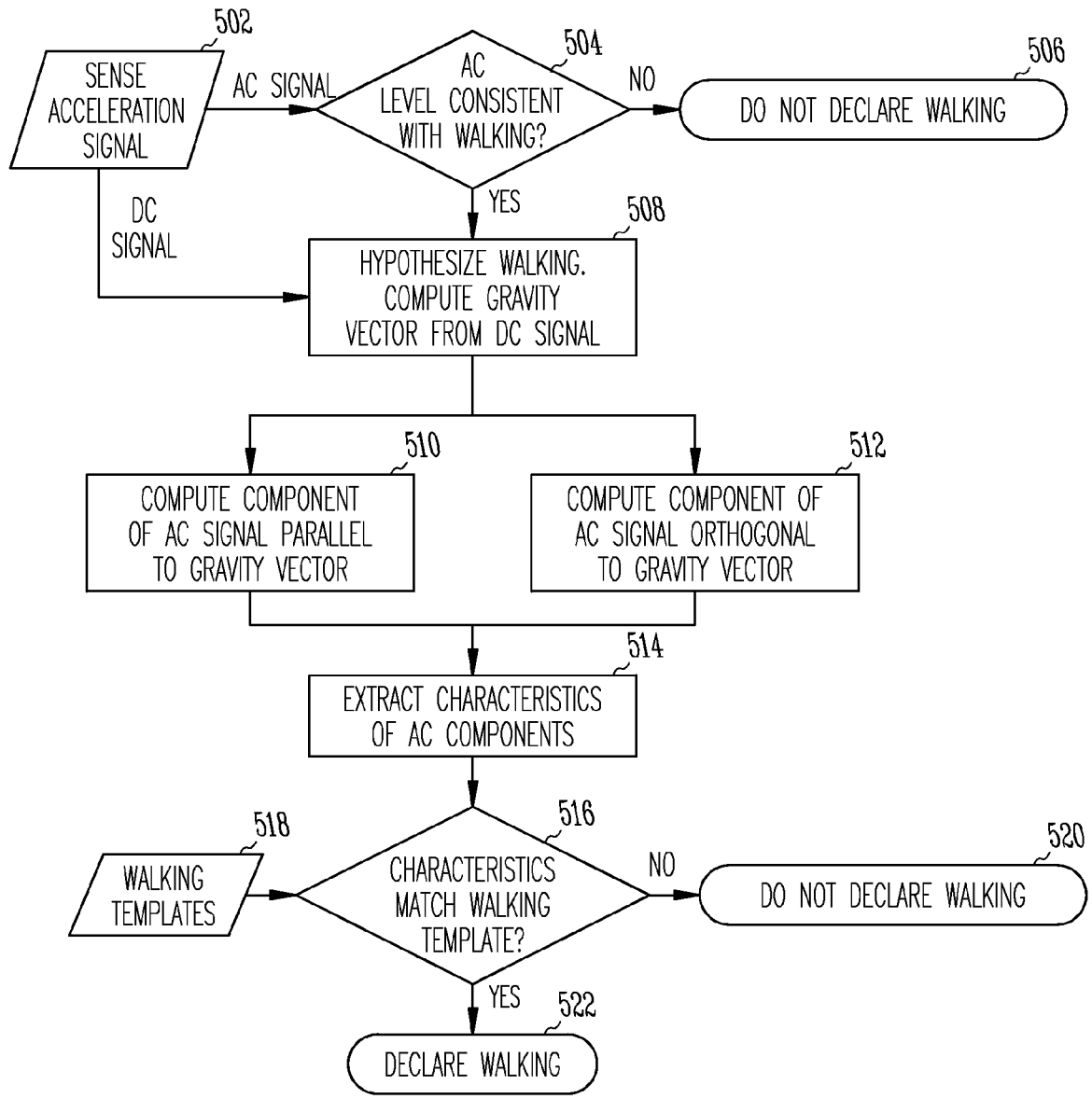
FIG. 5 is a flow chart illustrating an example of a method for detecting a walking state.

FIG. 5 is a flow chart illustrating an example of a method for detecting a walking state. At 502, an acceleration signal can be sensed from a patient, such as by using an implanted or external three-axis accelerometer. At 504, the AC component of the acceleration signal can be evaluated to determine whether it is consistent with walking or inconsistent with walking. In certain examples, this can include comparing an amplitude of the AC acceleration signal to a minimum amplitude threshold, such that if the AC amplitude exceeds the minimum amplitude threshold, walking is hypothesized. In certain examples, this can also include comparing the amplitude of the AC acceleration signal to a maximum amplitude threshold, such that walking is hypothesized when the AC amplitude exceeds the minimum amplitude threshold and is also below the maximum amplitude threshold. These comparisons can be made using a lumped vector sum magnitude of the individual 3D outputs of the 3D accelerometer, or can be made by comparing one or more individual 3D outputs of the 3D accelerometer to individual respective threshold values, and constructing a rule for combining the results of the three comparisons (e.g., x, y, z amplitudes all exceed their respective threshold values, 2 of 3 of the x, y, or z amplitudes exceed their respective threshold values etc.). In certain examples, a particular one (or a specified combination) of the x, y, or z outputs is used for the comparison. In certain examples, the amplitude comparison can be made using accelerometer signal amplitude in anterior or posterior directions, instead of other directions, such as to avoid possible noise due to accelerations in different directions (e.g., up-and-down acceleration due to riding in a car, elevator, etc.).

If the AC component of the acceleration signal is determined to be inconsistent with walking, at 506, a walking state is not declared. If at 504 the AC component of the acceleration signal is determined to be consistent with walking, a walking state is hypothesized at 508. In addition or alternative to the AC component of the acceleration signal, one or more other optional inputs can be used to hypothesize walking, such as a time of day consistent with walking, or a physiological state consistent with walking (see, e.g., John D. Hatlestad et al, U.S. patent application Ser. No. 11/466,925 (U.S. Pat. App. Publication No. 20080082001, now U.S. Pat. No. 8,343,049, which is incorporated herein by reference in its entirety). Examples of a time of day consistent with walking can include times when the patient is awake, such as during daytime hours (e.g. between 05:00 and 24:00). Other examples of a time of day consistent with walking can include times of the day during which walking was previously detected. Examples of a physiological state consistent with walking can include one or more of a detected heart rate, respiration rate, or blood pressure, the detected value being above a specified threshold. In a hypothesized walking state, a gravity vector can be computed from the DC component of the acceleration signal 508 in each of orthogonal x, y, and z directions of the accelerometer. At 510, a parallel component of the AC component of the acceleration signal (e.g., parallel to the direction of the gravity vector) can be computed. The parallel AC component can then be compared to a parallel AC template. At 512, an orthogonal component of the AC component of the acceleration signal (e.g., in a direction orthogonal to the gravity vector) can be computed. In an illustrative example, the orthogonal component can be computed by forming, in the plane that is orthogonal to the gravity vector, a set of two vectors that are orthogonal to each other and to the gravity vector. A vector sum of the AC component of the acceleration signal in the plane that is orthogonal to the gravity vector can be used as the orthogonal component of the AC component of the acceleration signal for comparing to a corresponding orthogonal AC template.

The orthogonal AC component can then be compared to an orthogonal AC template. The comparisons between the parallel AC component and the parallel AC template, and between the orthogonal AC component and the orthogonal AC template, can be used to distinguish the walking state from a non-walking activity. At 514, one or more characteristics of the orthogonal or parallel AC components can be extracted. Examples of characteristics of AC components include one or more frequency-domain characteristics, time-domain characteristics, and time-frequency-domain characteristics.

In a frequency domain example, a dominant signal amplitude of the (parallel or perpendicular component of the) AC signal can be extracted and its corresponding dominant signal frequency can be compared to a corresponding dominant signal frequency value of a template, and similarly, one or more higher harmonic frequencies of the dominant signal frequency can be compared to corresponding harmonic frequency values of the template.

In a time-domain example, a signal amplitude of the (parallel or perpendicular component of the) AC signal can similarly be extracted and compared to an amplitude of template. In another example, the shape of (parallel or perpendicular component of the) AC signal can be compared to a corresponding template, such as by performing a correlation between the signal and the template over a single or multiple periods, or between selected fiducial features of the signal and corresponding fiducial features of the template, or the like.

In a time-frequency domain example, a change in a frequency domain characteristic (e.g., dominant signal frequency) over time can be compared to a template value.

These frequency-domain characteristics, time-domain characteristics, and time-frequency-domain characteristics can be extracted for both the parallel component of the acceleration signal and the orthogonal component of the acceleration signal. Therefore, examples of such characteristics can include one or more of a parallel component frequency-domain characteristic, a parallel component time-domain characteristic, a parallel component time-frequency-domain characteristic, an orthogonal component frequency-domain characteristic, an orthogonal component time-domain characteristic, or an orthogonal component time-frequency-domain characteristic. At 516, one or more of such characteristics can be correlated or otherwise compared to one or more corresponding walking templates 518. The walking templates 518 can be patient-specific, or they can be generalized templates for use across a population or other plurality of patients. If the characteristics do not match the one or more walking templates, then walking is not declared at 520. If the characteristics match the one or more walking templates, then walking can be declared 522.

Figure 6:
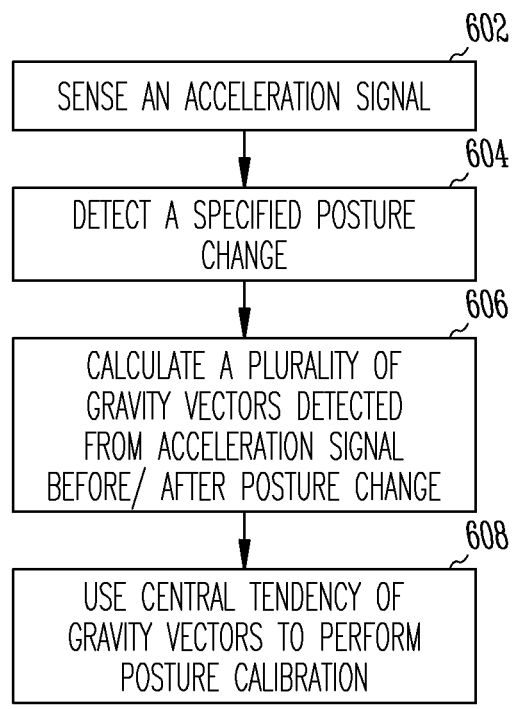
FIG. 6 is a flow chart illustrating an overview of an example of a method for performing posture calibration when a posture change is detected in a patient.

FIG. 6 is a flow chart illustrating an overview of an example of a method for performing posture calibration, such as when a posture change is detected in a patient. At 602, an acceleration or other posture-information including signal can be sensed from a patient, such as by using a three-axis accelerometer. At 604, one or more of a specified posture change can be detected, such as by looking for a specified change in the orientation of the DC component of the acceleration signal. At 606, a plurality of gravity vectors can be calculated, such as by using the gravity vectors detected from the acceleration signal during a time period that is before the specified posture change, or by using the gravity vectors detected from the acceleration signal during a time period that is after the specified posture change. A consistency of the gravity vectors during the specified time period, either before or after the posture change, can be determined. When the gravity vectors are deemed consistent, a central tendency of the gravity vectors during the specified time period, either before or after the posture change, can be used to perform a posture calibration at 608.

Figure 7:
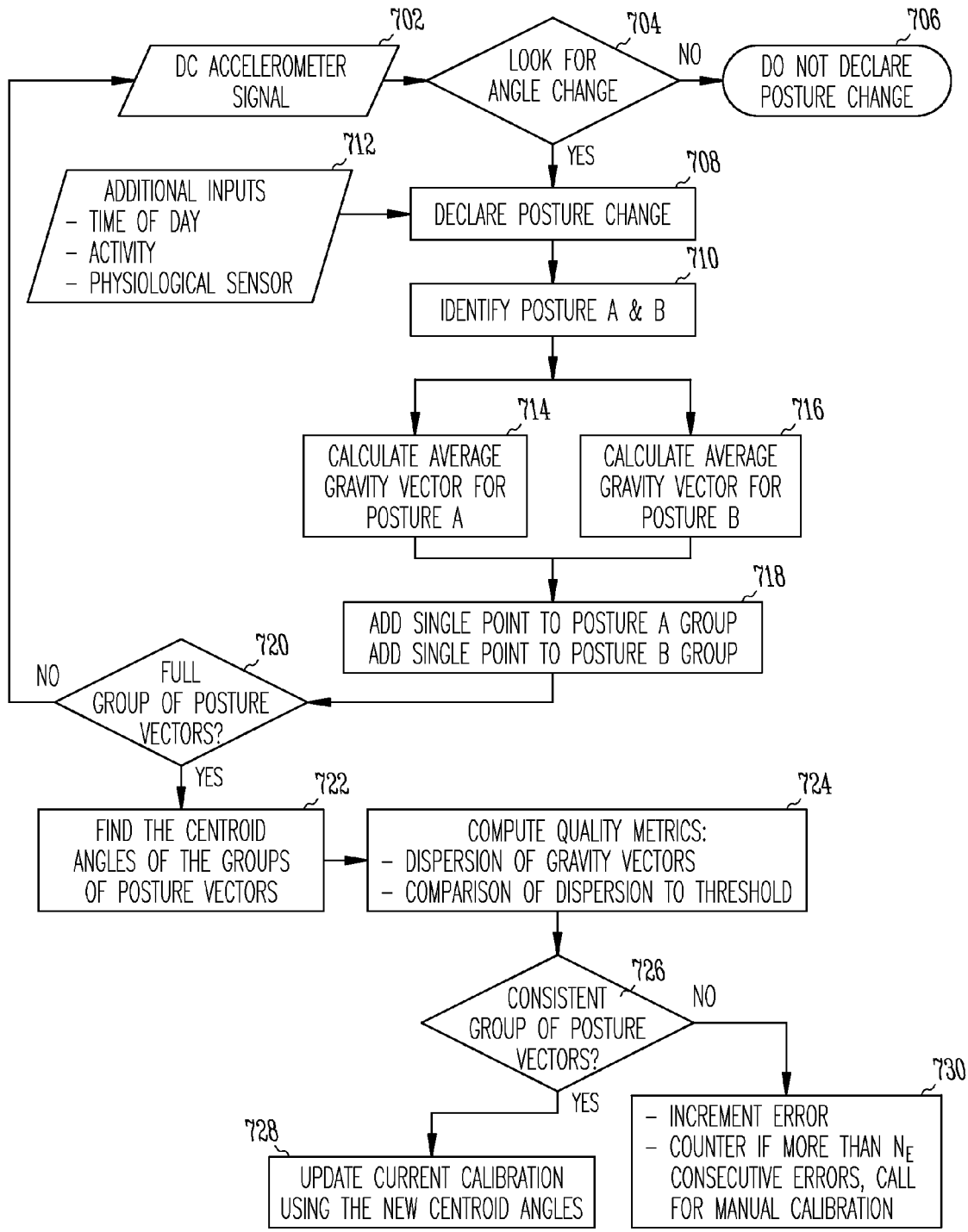
FIG. 7 is a flow chart illustrating an example of a method for detecting a posture change.

FIG. 7 is a flow chart illustrating an example of a method for detecting a posture change. At 702, the DC component of an acceleration signal from a patient can be computed, such as in each of orthogonal x, y, and z directions of a three-axis accelerometer. The DC component of the acceleration signal can be used to determine a gravity vector of the acceleration signal. At 704, a change in the orientation of the gravity vector of the acceleration signal is sought. If the angle change exceeds specified threshold value, a posture change can be declared at 708. If the angle change is not above the specified threshold value, no posture change is declared at 706. One or more other inputs at 712 can additionally or alternatively be optionally used to determine whether there has been a posture change. Examples of such additional inputs at 712 can include, by way of example, but not by way of limitation, a time of day consistent with a posture change, a physical activity level consistent with a posture change, or a physiological measurement consistent with a posture change (see, e.g., John D. Hatlestad et al, U.S. patent application Ser. No. 11/466,925 (U.S. Pat. App. Publication No. 20080082001), now U.S. Pat. No. 8,343,049, which is incorporated herein by reference in its entirety). For example, in the morning, when a patient gets up out of bed, the patient typically moves from a supine position to a sitting position, and then possibly to a standing position. These posture changes are typically accompanied by predictable changes in physical activity level, and can be accompanied by predictable changes in other physiological measurements, such as heart rate, respiration rate or blood pressure.

Once a posture change is declared at 708, a posture A and a posture B can be identified at 710. Posture A denotes the posture of the patient immediately before the posture change, and posture B denotes the posture of the patient immediately after the posture change. At 714, an average or other central tendency of a plurality of gravity vectors for posture A can be calculated. At 716, an average or other central tendency of a plurality of gravity vectors for posture B can be calculated. At 718, a single data vector for a gravity vector for posture A can be included in the group of posture A vectors, and a single data vector for a gravity vector for posture B can be included in the group of posture B vectors. The resulting groups of posture vectors can then be compared to a specified threshold number to determine whether the group is deemed complete or incomplete at 720. If the resulting groups of posture vectors are declared incomplete, then more data vectors are obtained for inclusion in the group. If the resulting groups of posture vectors are declared complete, the central tendencies (e.g. centroid orientation) of each group of postures vectors can be calculated at 722, such as to determine the consistency of the vectors within each group.

Determining the consistency of the gravity vectors for each posture, A and B, can include determining a central tendency of the gravity vectors, comparing the central tendency of the gravity vectors to a previously-determined central tendency of the gravity vectors, and determining whether the gravity vectors are consistent using a difference between the central tendency of the gravity vectors and the previously-determined central tendency of the gravity vectors. When the difference between the central tendency of the gravity vectors and the previously-determined central tendency of the gravity vectors exceeds a threshold value, the gravity vectors are deemed inconsistent. At 724, the consistency of the gravity vectors for each of posture A and posture B can be evaluated by determining the dispersion of the specified group of postures and comparing the dispersion to a specified dispersion threshold value. In some examples the dispersion may be computed using a previously-determined dispersion of the gravity vectors. At 726, the comparison of the dispersion of the specified group of postures to the specified dispersion threshold value can be used to determine whether the gravity vectors for the respective postures are consistent. A group of gravity vectors with a consistency above a specified threshold value is determined to be consistent 728. When a group of gravity vectors is deemed consistent, a central tendency measurement (e.g. centroid angles) of the consistent gravity vectors is used to perform a posture calibration of the acceleration signal of the accelerometer. When a group of gravity vectors is not deemed consistent 730, an error counter can be incremented. If the counter indicates that more than $N_E$ consecutive errors have occurred, an alert can be generated and communicated to a local or remote external user interface, so as to alert a user that manual calibration should be performed, instead of the automatic calibration described herein.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device comprising:
an accelerometer configured to sense an acceleration signal from a patient;
a filter circuit configured to extract a characteristic of the acceleration signal;
a comparison circuit configured to perform a comparison between the characteristic of the acceleration signal and a stored template to distinguish a walking state of the patient from a non-walking activity state of the patient; and
a posture calibration circuit configured to use an orientation of the accelerometer in the walking state to perform a posture calibration of the acceleration signal of the accelerometer.

2. The device of claim 1, wherein the filter circuit includes a highpass filter circuit configured to extract an AC component of the acceleration signal, the characteristic of the acceleration signal including a characteristic of the AC component of the acceleration signal.

3. The device of claim 1, comprising a communication circuit configured to:
receive posture calibration information from the posture calibration circuit; and
communicate the posture calibration information to an external local interface.

4. The device of claim 1, wherein the stored template includes a stored domain template, the domain being at least one of frequency, time, and time-frequency.

5. The device of claim 4, wherein the comparison circuit is configured to perform a comparison between the characteristic and the stored domain template, wherein the characteristic comprises a domain characteristic.

6. The device of claim 1, wherein the filter circuit includes a lowpass filter circuit configured to extract a DC component of the acceleration signal.

7. The device of claim 6, comprising a signal processor circuit configured to:
determine a gravity vector using the DC component of the acceleration signal;
compute a parallel component of the acceleration signal, the parallel component being in the direction of the gravity vector;
compute an orthogonal component of the acceleration signal, the orthogonal component being in a direction orthogonal to the gravity vector;
compare the parallel component to a parallel template and compare the orthogonal component to an orthogonal template; and
distinguish the walking state from the non-walking activity state using the computed parallel component of the acceleration signal and using the computed orthogonal component of the acceleration signal.

8. The device of claim 7, wherein the signal processor circuit configured to distinguish the walking state from the non-walking activity state includes:
determining a central tendency of the gravity vectors;
comparing the central tendency of the gravity vectors to a previously-determined central tendency of the gravity vectors; and
determining whether the gravity vectors are consistent using a difference between the central tendency of the gravity vectors and the previously-determined central tendency of the gravity vectors.

9. A device comprising:
an accelerometer configured to sense an acceleration signal from a patient;
a first filter circuit configured to extract a first component of the acceleration signal;
a comparison circuit configured to perform a comparison between a characteristic of the first component of the acceleration signal and a stored template to distinguish a walking state of the patient from a non-walking activity state of the patient;
a second filter circuit configured to extract a second component of the acceleration signal;
a signal processor circuit configured to:
determine a gravity vector using the second component of the acceleration signal;
compute a parallel component of the acceleration signal, the parallel component being in the direction of the gravity vector;
compute an orthogonal component of the acceleration signal, the orthogonal component being in a direction orthogonal to the gravity vector;
compare the parallel component to a parallel template and compare the orthogonal component to an orthogonal template; and
distinguish the walking state from the non-walking activity state using the computed parallel component of the acceleration signal and using the computed orthogonal component of the acceleration signal; and
a posture calibration circuit configured to use an orientation of the accelerometer in the walking state to perform a posture calibration of the acceleration signal of the accelerometer.

10. The device of claim 9, wherein the first filter circuit includes a highpass filter circuit, the first component including an AC component of the acceleration signal.

11. The device of claim 9, wherein the second filter circuit includes a lowpass filter circuit, the second component including a DC component of the acceleration signal.

12. The device of claim 9, wherein the signal processor circuit configured to distinguish the walking state from the non-walking activity state includes:
determining a central tendency of the gravity vectors;
comparing the central tendency of the gravity vectors to a previously-determined central tendency of the gravity vectors; and
determining whether the gravity vectors are consistent using a difference between the central tendency of the gravity vectors and the previously-determined central tendency of the gravity vectors.

13. The device of claim 9, comprising a communication circuit configured to:
receive posture calibration information from the posture calibration circuit; and
communicate the posture calibration information to an external local interface.

14. A system comprising:
a device comprising:
an accelerometer configured to sense an acceleration signal from a patient;
a filter circuit configured to extract a characteristic of the acceleration signal;
a comparison circuit configured to perform a comparison between the characteristic of the acceleration signal and a stored template to distinguish a walking state of the patient from a non-walking activity state of the patient;

a posture calibration circuit configured to use an orientation of the accelerometer in the walking state to perform a posture calibration of the acceleration signal of the accelerometer; and a communication circuit configured to receive posture calibration information from the posture calibration circuit; and an external local interface configured to receive the posture calibration information from the communication circuit.

15. The system of claim 14, wherein the device includes an implantable cardiac function management device.

16. The system of claim 14, wherein the filter circuit includes a highpass filter circuit configured to extract an AC component of the acceleration signal, the characteristic of the acceleration signal including a characteristic of the AC component of the acceleration signal.

17. The system of claim 14, wherein the external local interface is configured to wirelessly bidirectionally communicate with the communication circuit.

18. The system of claim 14, comprising an external remote interface configured to bidirectionally communicate with the external local interface.

19. The system of claim 14, wherein the filter circuit includes a lowpass filter circuit configured to extract a DC component of the acceleration signal.

20. The system of claim 19, wherein the device includes a signal processor circuit configured to:

determine a gravity vector using the DC component of the acceleration signal;

compute a parallel component of the acceleration signal, the parallel component being in the direction of the gravity vector;

compute an orthogonal component of the acceleration signal, the orthogonal component being in a direction orthogonal to the gravity vector;

compare the parallel component to a parallel template and compare the orthogonal component to an orthogonal template; and distinguish the walking state from the non-walking activity state using the computed parallel component of the acceleration signal and using the computed orthogonal component of the acceleration signal.

* * * * *